United States Patent [19]

Meehan

[11] Patent Number: 4,567,613
[45] Date of Patent: Feb. 4, 1986

[54] METHOD AND ARTICLE FOR NEUTRALIZING OFFENSIVE ODORS

[76] Inventor: Frank Meehan, 203 Cathedral Ave., Hempstead, N.Y. 11550

[21] Appl. No.: 608,185

[22] Filed: May 8, 1984

[51] Int. Cl.$^4$ ............................................... E03D 9/02
[52] U.S. Cl. ........................................ 4/209 R; 4/222; 4/309; 4/661
[58] Field of Search .............. 422/41; 424/76; 236/79; 4/222, 209 R, 223, 220, 309, 661, 213

[56] References Cited

U.S. PATENT DOCUMENTS

| | | | |
|---|---|---|---|
| 721,909 | 3/1903 | Norris ........................................ | 4/223 |
| 1,075,210 | 10/1913 | Heyl et al. ............................ | 206/0.5 |
| 2,470,851 | 5/1949 | Hermanson ................ | 401/201 R X |
| 2,700,461 | 1/1952 | Smith .................... | 206/219 |
| 2,717,174 | 9/1951 | Casanovas ............................ | 239/56 |
| 3,146,929 | 9/1962 | Keim ................ | 229/2.5 R |
| 3,198,251 | 8/1965 | Shore .................... | 424/76 |
| 3,549,381 | 12/1970 | Kinsinger ............................ | 426/77 |
| 3,597,772 | 8/1971 | Leavitt et al. ............................ | 4/222 |
| 3,619,462 | 11/1971 | Dines et al. .................... | 264/300 |
| 3,623,659 | 11/1971 | Maierson et al. ............................ | 239/56 |
| 3,655,129 | 4/1972 | Seiner ............................ | 239/56 |
| 3,685,734 | 8/1972 | Paciorek et al. ............................ | 239/56 |
| 3,762,875 | 10/1973 | Burmeister ............................ | 422/41 |
| 3,775,334 | 11/1973 | Christie ............................ | 252/17 |
| 3,785,536 | 1/1974 | Graham ............................ | 239/34 |
| 3,823,816 | 7/1974 | Controulis et al. ................ | 206/0.5 |
| 3,865,603 | 2/1975 | Szymanski et al. ................ | 106/130 |
| 3,885,737 | 5/1975 | Watkins ............................ | 239/34 |
| 3,892,905 | 7/1975 | Albert ............................ | 428/220 |
| 3,917,116 | 11/1975 | Mason ............................ | 222/92 |
| 4,017,030 | 4/1977 | Coplan et al. ............................ | 239/44 |
| 4,037,716 | 7/1977 | Marks ............................ | 206/38 |
| 4,055,668 | 10/1977 | Kopp ............................ | 426/79 |
| 4,103,367 | 8/1978 | Kaufer ............................ | 4/222 |
| 4,127,383 | 11/1978 | Johnston et al. ............................ | 21/55 |
| 4,130,245 | 12/1978 | Bryson ............................ | 239/34 |
| 4,188,304 | 2/1980 | Clarke et al. ............................ | 252/93 |
| 4,260,054 | 4/1981 | Bory et al. ............................ | 206/0.5 |
| 4,296,179 | 10/1981 | Wardwell ............................ | 428/498 |
| 4,367,203 | 1/1983 | Landsberger ............................ | 422/305 |

*Primary Examiner*—Henry K. Artis
*Attorney, Agent, or Firm*—Roberts, Spiecens & Cohen

[57] ABSTRACT

A disposable article for neutralizing offensive odors comprising a sheet of foldable material having a fold-line dividing the sheet into first and second portions. At least one of the portions has a grid region therein for adsorption of an odor-neutralizing liquid. The portions are folded into confronting relation after adsorption of the liquid in the grid region and the sheet is sealed around the grid in a manner to be subsequently peeled open to expose the adsorbed liquid to the ambient atmosphere at the time of use. The fold-line applies a slight bias to the first and second portions when opened to oppose complete unfolding of the portions into a flat state.

18 Claims, 7 Drawing Figures

METHOD AND ARTICLE FOR NEUTRALIZING OFFENSIVE ODORS

FIELD OF THE INVENTION

The invention relates to a throwaway article and associated method for neutralizing offensive odors, particularly those produced by fecal matter.

The invention has particular applicability to use in toilets and, particularly, where disposal may not be immediate such as in bedpans and portable toilets and on small boats, busses, and the like.

The invention also has special applicability to use in small quarters with poor ventilation.

MATERIAL INFORMATION STATEMENT

Pursuant to Applicant's duty of disclosure in accordance with 37 C.F.R. 1.56 and consistent with 37 C.F.R. 1.97–1.99, Applicant would like to make of record the references which are listed on the attached form PTO 1449.

Each of Heyle et al, Keim, Kissinger, Bryson, Borey et al and Hermanson show packaging structures which contain multiple cells wherein each cell can be filled with a small amount of material. In Heyl et al the outer wrapper is soluble in a liquid to which the contents of the package are to be added. The packaging material in Heyl et al is gelatin.

Bryson forms his package of a plastic material which is permeable to a liquid within the package so that the liquid can escape gradually.

Keim shows a cellular package held together by tongue and groove arrangement.

Kissinger shows a package made of a thermoplastic film which will open to a net-like structure when it is mechanically stretched. The laundry additive package of Bory et al opens by being torn along a line of perforations to release the additive to the water.

Maierson et al, Seiner, Controulis et al, Paciorek et al, and Coplan et al all show containers providing for gradual release of vapors.

Norris, Leavitt et al, Christie and Kaufer all show deodorizers designed to work gradually.

Landsberger shows a heat released deodorant.

Seiner and Szymanski et al disclose gelatin films, which are used to package such items as deodorants. Albert shows a cold water soluble film.

Kopp and Smith each show containers which are folded initially and are unfolded in use to dispense substances into a surrounding liquid.

Wardwell, Clarke et al and Mason show packaging for liquids and Graham, Casanovas and Dines show additional ways of packaging a volatile material. Marks shows a package with an adhesively coated lid.

Burmeister shows the use of an article added to water in a toilet bowl to form an odor-sealing foam cushion before using the toilet. Johnston et al show particular foaming agents.

Shore discloses water-dispersible or water-soluble deodorant preparations.

SUMMARY OF THE INVENTION

Despite the well known features in the body of art disclosed hereinabove, there is need for the use of an article which can be readily stored and employed in use before generation of an odor in order to counteract the odor.

An important deficiency in the known art is the absence of an article which is capable of use both in the presence or absence of water.

An object of the invention is to provide an inexpensive package and associated method which will overcome the disadvantages of the known art and enable use in toilet facilities with or without water.

A further object of the invention is to provide a throwaway package which is relatively inexpensive and which is capable of being carried for activation at the time of use.

Yet another object of the invention is to provide a throwaway package which will allow itself to be activated without contaminating either the user or his or her surroundings.

Still another object of the invention is to provide a throwaway article of the above character which employs a minimal quantity of active substance and which is readily disposable and is biodegradable.

Still another object of the invention is to provide a throwaway article of the above character which is openable by peeling and which is introduced into the toilet facility prior to use and is thereafter flushed away, leaving no scent behind.

In accordance with the above, and further objects of the invention, there is provided a throwaway article for neutralizing offensive odors which comprises a sheet of foldable material having a fold-line dividing the sheet to first and second portions, at least one of which includes a grid region therein on which an odor neutralizing liquid is adsorbed. The sheet is folded about the fold line to bring the first and second portions in confronting relation so that the article is ready for use. The sheet of foldable material is impervious to the odor-neutralizing liquid to prevent leakage thereof through the material and dissipation of any odor thereof.

The seal of the sheet is peelable to permit the user to open the package and expose the odor neutralizing liquid adsorbed in the grid region.

The fold line joining the first and second portions of the sheet applies a slight bias to the first and second portions to oppose complete unfolding of the portions into a flat state so that the unfolded sheet will have a slight V-shaped configuration. Thereby, if the unfolded sheet is deposited face down on a flat surface the grid region with adsorbed liquid will be disposed above the flat surface and thereby capable of releasing the odor neutralizing liquid to the ambient atmosphere.

In accordance with a feature of the invention, preferably the sheet of foldable material is biodegradable such as gelatin.

In accordance with a further feature of the invention, the odor neutralizing liquid is contained in a petroleum base which is lighter than water and highly dispersable therein so that the liquid will be broken into a multitude of droplets which will be dispersed on the surface of the water.

An essential aspect of the invention is that the package and its associated method of use does not contemplate after usage in the manner of conventional coverup sprays and leave a residual odor which in many cases, itself is offensive but, rather, is readied for use by the simple act of opening the package and depositing the same into the toilet facility after which it is removed along with the offensive material. The odor neutralizing liquid directly counteracts the offensive odor in a generally substantially confined environment.

DETAILED DESCRIPTION OF THE PREFERRED EMBODIMENT

Figure 2:
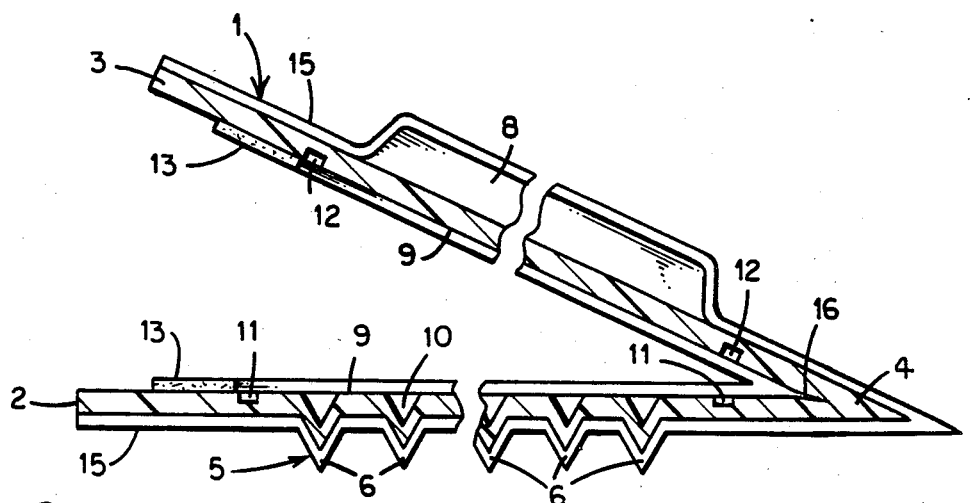
FIG. 2 is a sectional view taken along line II—II with the throwaway article partially folded towards the closed state.

In the drawing is illustrated a throwaway or disposable article 1 for neutralizing offensive odors. The article 1 comprises a sheet of material having portions 2 and 3 foldably joined at a fold line or hinge 4. The hinge 4 is formed by removing material at the join line of portions 2 and 3 so that the portions can be folded into confronting relation as shown in FIG. 2 where the article is in the partially folded state.

Portion 2 includes a grid region 5 composed of a series of parallel crenalations 6 adapted for adsorbing liquid, as will be explained more fully later. The portion 3 also includes a grid region 7 whose crenalations 8 extend in a direction perpendicular to crenalations 6.

When the portions 2 and 3 are folded into confronting relation, flat surfaces 9 of the portions in the grid regions 5 and 7 will come into confronting relation in order to substantially isolate the hollows 10 of the crenalations in which the liquid is contained. In this way, the adsorbed liquid will be divided up into multitudes of miniscule droplets which will be readily adsorbed in the hollows.

The crenalations in the grid regions 5 and 7 expand the surface area of the portions 2 and 3 of the sheet to break up the liquid droplet so that it can be adsorbed over the surface area as a non-flowable film in the confined region. As a consequence, when the article is opened, the liquid will not splatter on the user.

Under certain circumstances, it may be possible to utilize only one grid on one portion and instead of the illustrated construction of the grid formed by the crenalations, it may be possible to provide a surface treatment of the material such as by roughening the surface thereof to achieve the adsorbtion of the liquid.

Encircling the grid region 5 is a continuous groove 11, while surrounding the grid region 7 is a continuous groove 12. The grooves 11 and 12 isolate the grid regions 5 and 7 and the liquid therein from the remainder of the article for a purpose which will become evident hereafter.

Surrounding the grid regions in both portions 2 and 3 is an adhesive border 13. When the sheet is folded around hinge 4, the adhesive border seals itself by contact at both portions. It is noted that the grooves 11 and 12 isolate the adhesive border 13 in order to prevent any contact between the liquid in the grid regions and the adhesive. The grooves 11 and 12 also flank the hinge 4 to prevent any penetration of liquid to the hinge which could lead to splatter upon opening of the article.

When the article is closed and the adhesive border 13 has been brought into contact from both portions, the article is in readiness for use. A pair of bare tabs 14 are formed at the opposite ends to serve as an engagement means which will allow the user to open the article. The adhesive in the border 13 allows the article to be opened by application of separating pressure to the tabs 14.

The material of the article 1 can be of wide ranging composition provided that it is impermeable to the liquid which is adsorbed in the grid regions. Moreover, not only must it be impermeable to the liquid, it must also be impermeable to the deodorant smell thereof. A suitable material for the sheet of the article is PET film and it can have a thickness of the order of 0.003 to 0.010 inches. Different materials may have different thicknesses and the thickness can also vary as a function of the liquid which is adsorbed in the grid regions. There are numerous pressure-sensitive peelable adhesives for PET material currently available on the market, as will be wellknown to those skilled in the art and not requiring any elaboration herein.

According to a feature of the invention, the sheet material of the article 1 can advantageously be made of a hardened gelatin so that it will be biodegradable. The closure of the portions at the adherent border 13 can be made by forming a moisture or heat seal between the portions. Thereby, the portions become firmly joined together to form an airtight non-permeable seal which nevertheless is openable to gain access to the grid regions 5 and 7 in use. When the material of the article 1 is composed of gelatin, this is coated with a layer of biodegradable paper 15 to inhibit the exposure of the gelatin and minimize moisture degradation as well as inhibit heat transfer and consequent premature melting. Preferably, a taste offensive substance is placed into the coating to prevent ingestion by children and animals. The taste offensive substance can be a bitter flavoring material alum, peppers, a concentrate of sweeteners, or the like. The taste offensive substance must also be non-staining. If desired, the entire article 1 can be packed in its own cellophane packet.

The liquid which is adsorbed in the grid regions 5 and 7 is intended to serve the function of neutralizing offensive odors, particularly those produced by human fecal matter, and it is intended that the entire article 1 be opened at the time of use to expose the adsorbed liquid in the grid regions to the ambient atmosphere prior to use of a toilet facility. The liquid comprises a potent volatile deodorant which is capable of nullifying offensive odors and various substances are adaptable for this purpose. By way of example, an applicable deodorant liquid is available under the trademark "SCENT-GO" manufactured by the Scenoret Chemical Company of Kirkwood, Mo. The deodorant is based on petroleum distillates and ortho dichlorobenzene which is effective to keep the deodorant in floating state on water in highly dispersed droplet form. As a consequence, the deodorant will be extremely effective when the article 1 is opened and dropped into a toilet bowl.

According to the conception of the invention, the article 1 is utilized prior to evacuation by opening the article and depositing it into the facility which is to be used. Generally, the product acts in a captive atmosphere and the deodorant is effective by molecular reaction to destroy the malodorous smell. When the toilet is flushed, the article 1 is removed and there is no lingering deodorant scent, as in the case of conventional sprays and slow-release liquids. Indeed, such scents themselves frequently are offensive to the users.

Figure 3:
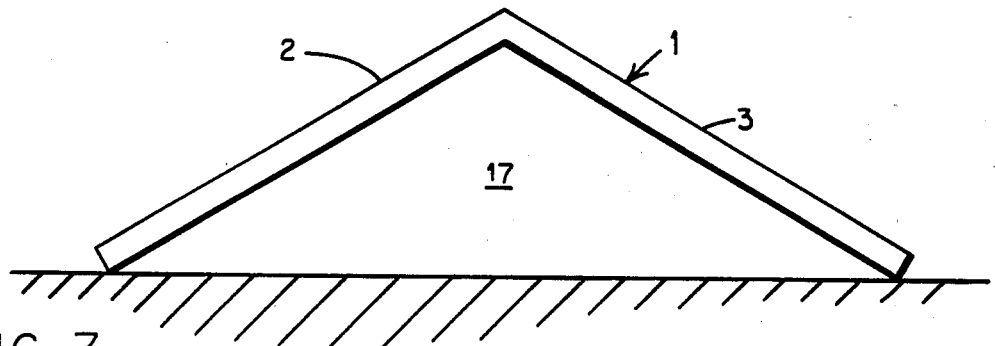
FIG. 3 is a diagrammatic illustration showing the article in unfolded ready to use state after it has been deposited on a flat surface.

Since it is also contemplated for the article 1 to be utilized under non-aqueous conditions, such as bedpans, it is important that the article when opened not be capable of being rendered ineffective such as by a smothering action on the adsorbed liquid in the grid regions. For this purpose, the hinge or foldline 4 is constructed so that it opposes opening of the portions 2 and 3 into a flat condition. This is achieved for the material of the invention when it is provided with the thickness previously indicated and with the formation of a shallow V-groove 16 for the formation of the hinge wherein the remaining thickness of the material at the groove 16 is a minor portion of the thickness of the material. As a consequence, there will be a natural bias built into the material tending to return it to a partially folded position whereby if the article lands face down, as shown in FIG. 3, there will be a space 17 formed beneath the article to allow circulation of air so that the adsorbed liquid can serve the deodorant function.

Although the invention has been described in relation to a specific embodiment thereof, it will be obvious to those skilled in the art that numerous modifications and variations can be made without departing from the scope and spirit of the invention. Thus, the grooves 11 and 12 which have been illustrated in both portions 2 and 3 of the sheet of the article could be formed as tongue and groove arrangements. Also, while both grid regions have been illustrated as being formed of crenelations, it is also possible to make one region depressed and the other region projecting.

Figure 4:
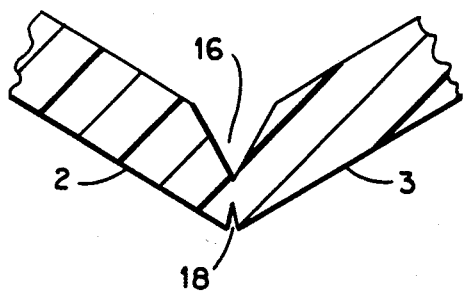
FIG. 4 is a view of a modified portion of the hinge of the article of FIGS. 1–3 on enlarged scale.

In order to insure that the article 1 will not be opened flat which could lead to blockage of the adsorbed liquid, other modifications could be used in replacement of the biassed hinge 4 of the described embodiment. For example, a stop could be built into the sheet to prevent its unfolding to flat condition as shown in FIG. 4 where the stop is formed of a narrow slit 18 in the back surface of the article below the groove 16.

Figure 5:
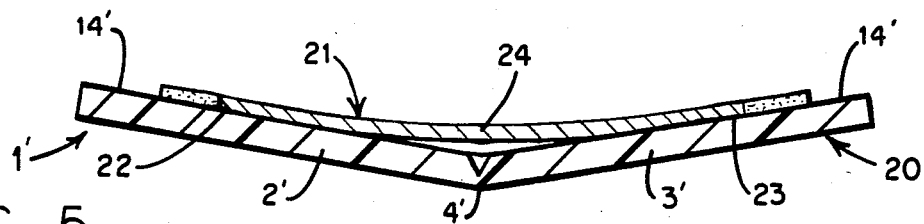
FIG. 5 is a sectional view of a modified embodiment of the article of the invention.
Figure 6:
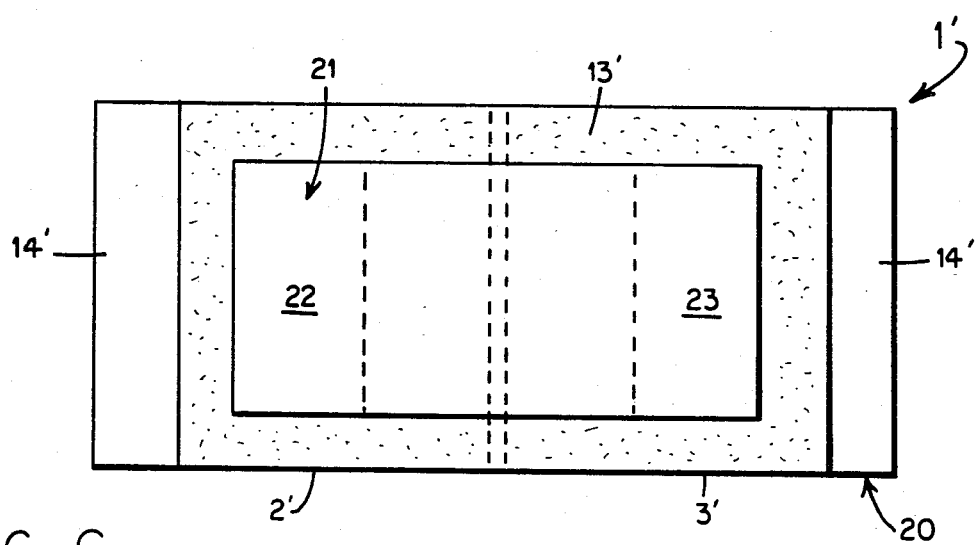
FIG. 6 is a plan view of the article of FIG. 5.

In another modification illustrated in FIGS. 5 and 6, the article is designated by numeral 1' and is formed of two portions 2' and 3' hinged at 4'. The portions 2' and 3' are formed from a flat sheet 20 of plastic material such as PET and a peelable adhesive 13' is provided in the border region thereof in the manner illustrated in FIG. 6. However, instead of forming the grid regions with the adsorbed liquid therein as in FIG. 1, a separate sheet 21 of absorbent material such as porous paper is employed both for absorption of the deodorant liquid and as a means for preventing the sheet of plastic material from being folded into flat condition. Thus, as shown in FIGS. 5 and 6, the sheet 21 is affixed to the sheet 20 at spaced regions 22 and 23 and is unattached in region 24 such that the sheet 20 can only be opened to the partially unfolded state shown in FIG. 5, further opening of sheet 20 being resisted by sheet 21. The article 1' is used in the same manner as that of article 1 insofar that in use the article 1' is opened by grasping bare tabs 14' and unpeeling the portions along adhesive border 13 to expose the sheet 21 containing the absorbed deodorant. The article 1' is deposited into a toilet facility and if the facility contains water, the deodorant liquid will become dispersed therein in preparation for a deodorizing operation. As before, the article will be flushed away with the odorous material.

Figure 1:
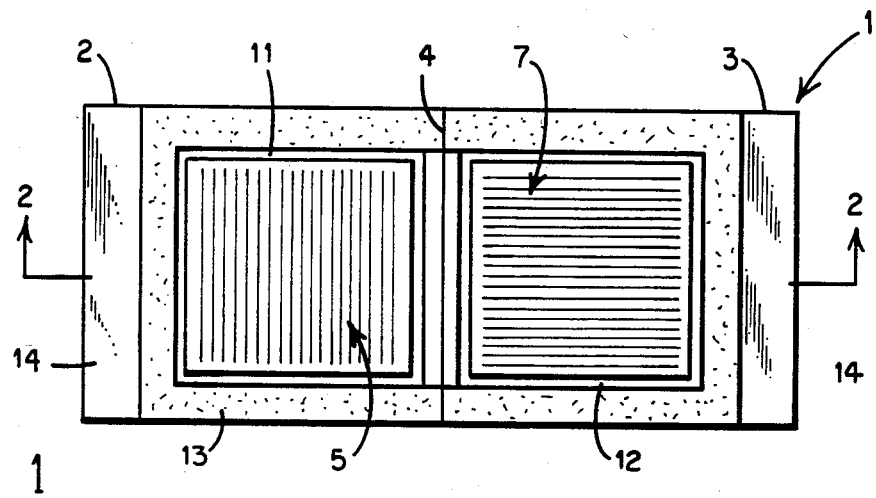
FIG. 1 is a plan view showing an embodiment of the article of the invention in opened state.
Figure 7:
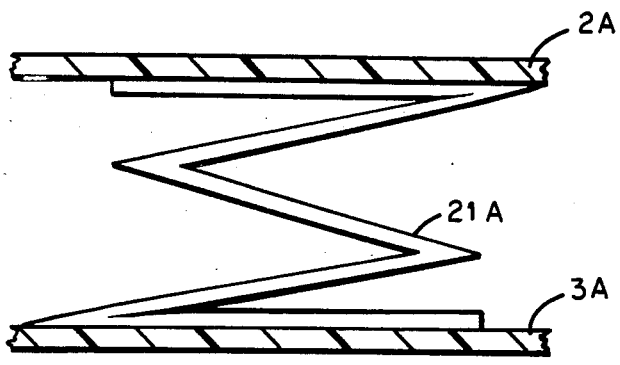
FIG. 7 is a sectional view of another modified embodiment of the article of the invention.

A modification is shown in FIG. 7 wherein instead of hinging portions together as in FIGS. 1 and 5, the portions are disconnected as shown at 2A and 3A and joined by a sheet 21A of absorbent material containing deodorant liquid. The sheet 21A is folded accordion style and the portions 2A and 3A are joined by peelable adhesive surrounding sheet 21A. In order to prepare the article for use the portions 2A and 3A are separated by peeling the adhesive and the sheet 21A is unfolded by pulling the portions 2A and 3A away from one another. The article is now ready for use in the manner previously described.

I claim:

1. A throw-away article for neutralizing offensive odors, said article comprising a sheet of foldable material having a fold line dividing the sheet into first and second portions, at least one of said portions including a grid region therein adapted for adsorption of a liquid, an odor-neutralizing liquid adsorbed in said grid region, and seal means on said sheet sealing the sheet in folded condition with the first and second portions in confronting relation, said sheet of foldable material being impervious to the odor-neutralizing liquid to prevent leakage thereof through the material and dissipation of any odor thereof, said seal means being peelable to permit a user to open the sheet of material and expose the odor-neutralizing liquid adsorbed in said region, said fold line applying a slight bias to said first and second portions to oppose complete unfolding of the portions into a flat state and producing a slight V-shape configuration for the unfolded portions so that if the unfolded sheet of material is deposited face down on a flat surface said grid region with adsorbed liquid will be disposed above the flat surface.

2. A throw-away article as claimed in claim 1, wherein said sheet of foldable material is biodegradable.

3. A throw-away article as claimed in claim 2, wherein said biodegradable sheet of material is gelatin.

4. A throw-away article as claimed in claim 3, comprising a biodegradable sheet of paper coating said gelatin.

5. A throw-away article as claimed in claim 4, comprising a taste offensive substance in said coating sheet.

6. A throw-away article as claimed in claim 1, wherein said seal means comprises a peelable adhesive which forms an air-tight, liquid impermeable seal.

7. A throw-away article as claimed in claim 1, wherein said grid region comprises dentalations in said sheet of material.

8. A throw-away article as claimed in claim 7, wherein said dentalations are provided in both of said portions.

9. A throw-away article as claimed in claim 8, wherein the dentalations in said portions extend in perpendicular relation to one another.

10. A throw-away article as claimed in claim 1, comprising groove means in said sheet of material for preventing said liquid in said grid region from flowing to said fold line and to said seal means.

11. A throw-away article for neutralizing offensive odors, said article comprising a sheet of material including first and second portions, means connected to said portions containing an odor-neutralizing liquid, seal means sealing said first and second portions in confronting relation with said means enclosed therein, said sheet of material being impervious to the odor-neutralizing liquid to prevent leakage thereof through the material and dissipation of any odor thereof, said seal means being peelable to permit a user to separate said portions and expose the odor-neutralizing liquid, said means which connects said portions preventing said portions from assuming a flat coplanar state so that if the sheet of material is deposited onto a flat surface, said means with odor-neutralizing liquid will be exposed to the ambient air and disposed above the flat surface.

12. A throw-away article as claimed in claim 1, wherein said means which connects said portions comprises a sheet of material folded in accordion fashion.

13. A throw-away article as claimed in claim 11, wherein said seal means comprises a peelable adhesive which forms an air-tight, liquid impermeable seal.

14. A throw-away article for neutralizing offensive odors, said article comprising a sheet of foldable material having a fold line dividing the sheet into first and second portions, means connecting said portions and adapted for containing an odor-neutralizing liquid, seal means on said sheet sealing the sheet in folded condition with the first and second portions in confronting relation, said sheet of foldable material being impervious to the odor-neutralizing liquid to prevent leakage thereof through the material and dissipation of any odor thereof, said seal means being peelable to permit a user to open the sheet of material and expose the odor-neutralizing liquid, said means which connects said portions preventing complete unfolding of said portions into a flat state and producing a slight V-shape configuration for the unfolded portions so that if the unfolded sheet of material is deposited face down on a flat surface, said means with the liquid will be disposed above the flat surface.

15. A throw-away article as claimed in claim 14, wherein said means which connects said portions comprises a second sheet of material having ends affixed to the first said sheet of material and a central region unattached to the first said sheet.

16. A method of neutralizing offensive odors produced by human evacuation into a toilet facility, said method comprising forming a throw-away article by folding a sheet of material along a fold line to superimpose first and second portions of the sheet of material on one another, one of said portions having an odor-neutralizing substance contained in a region thereof, and sealing the folded sheet around the edges thereof with a peelable sealing material, opening the sealed folded sheet by unpeeling the edges thereof and unfolding the sheet to expose the odor-neutralizing substance to the ambient air, and depositing the opened article into the toilet facility prior to evacuation thereinto so that said neutralizing substance will neutralize offensive odors of the subsequent evacuation, said fold line applying a slight bias to said first and second portions of said sheet of material to oppose complete unfolding of said portions into a flat state and producing a slight V-shape configuration for the unfolded portions so that if the unfolded sheet of material is deposited face down on a flat surface said region with the odor-neutralizing substance will be disposed above the flat surface.

17. A method according to claim 16 wherein the toilet facility contains water and the sheet of material is soluble in the water.

18. The method according to claim 16 wherein said toilet facility contains water and said odor-neutralizing substance is a liquid which is dispersable in floating relation on the surface of the water.

* * * * *